United States Patent [19]

Chaoui

[11] Patent Number: 4,494,252
[45] Date of Patent: Jan. 22, 1985

[54] LARYNGEAL PROSTHESIS

[75] Inventor: Samir M. Chaoui, Placentia, Calif.

[73] Assignee: Bear Medical Systems, Inc., Riverside, Calif.

[21] Appl. No.: 525,306

[22] Filed: Aug. 22, 1983

[51] Int. Cl.³ .............................................. A61F 1/20
[52] U.S. Cl. ................................. 3/1.3; 128/207.16; 128/207.17
[58] Field of Search .................... 3/1.3; 128/207.14

[56] References Cited

U.S. PATENT DOCUMENTS

| | | | |
|---|---|---|---|
| 3,747,127 | 7/1973 | Taub | 3/1.3 |
| 3,952,335 | 4/1976 | Sorce et al. | 3/1.3 |
| 4,060,856 | 12/1977 | Edwards | 3/1.3 |
| 4,223,411 | 9/1980 | Schoendorfer et al. | 3/1.3 |
| 4,274,162 | 6/1981 | Joy et al. | 3/1.3 |

FOREIGN PATENT DOCUMENTS

0078685  5/1983  European Pat. Off. .............. 3/1.3

Primary Examiner—Richard J. Apley
Assistant Examiner—James Prizant
Attorney, Agent, or Firm—Howard J. Klein

[57] ABSTRACT

An external, self-contained laryngeal prosthesis is adapted for use by a tracheostomized patient having a surgically-formed "pseudoglottis" separating the trachea and the hypopharynx. The prosthesis includes a housing and a fitting for attaching the housing to the tracheostoma formed in the patient's neck. The housing contains an inhalation valve to allow inhaled air to pass through a first conduit into the trachea, and an exhalation valve for directing exhaled air from the first conduit into the housing downstream from the inhalation valve toward a second conduit. The second conduit is adapted for communicating between the housing and the hypopharynx through the fitting and through an incision in the pseudoglottis. Downstream from the exhalation valve is a tone-generating mechanism responsive to air pressures in a range normally produced by a speech effort. At higher air pressures, such as produced by panting or gasping, the tone-generating mechanism is disabled, and an alternative air flow path from the exhalation valve to the second conduit is opened.

27 Claims, 5 Drawing Figures

LARYNGEAL PROSTHESIS

BACKGROUND OF THE INVENTION

This invention relates generally to the field of laryngeal prostheses. In particular, it relates to a laryngeal prosthesis which can discriminate between an exhalation effort and a phonation effort, in a manner analogous to the natural larynx.

The larynx performs two functions. First, it contains the vocal chords, by means of which vocal sounds are produced. Of equal importance, the larynx includes a movable tissue, the epiglottis, which prevents food and liquids from entering the trachea from the mouth.

Disease or injury may require the removal of the larynx by a surgical procedure known as a laryngectomy. As a result of the laryngectomy, the patient is left with an opening, or tracheostoma, directly into the trachea from the front of the neck, and the patient can then exhale and inhale through the tracheostoma. Because the epiglottis is also removed, a barrier or "pseudoglottis" between the pharynx and the trachea is provided by suturing the tracheal-esophageal wall to the interior tissue of the neck, covering the normal tracheal opening into the hypopharyngeal cavity.

The laryngectomized patient is thus left without the usual means to produce speech. In some patients, the speech function can be restored by a technique known as esophageal speech. This technique is difficult to master, and is, therefore, of benefit only to the minority of patients who can successfully learn it. Even so, the sound produced is not altogether natural.

Consequently, efforts have been made to produce an artificial larynx, or laryngeal prosthesis, to provide a speech function more closely approaching that of the natural larynx. In this regard, several approaches have been taken.

One common approach may be generally termed the "external laryngeal prosthesis." Typically, such a prosthesis includes a valve assembly, mounted external to the tracheostoma, which allows normal breathing therethrough. For speaking, such devices include means for diverting air into the lower regions of the vocal tract, such as the hypopharyngeal cavity, in the vicinity of the area formerly occupied by the larynx. This diverted air flow can be used to form vocalized sounds, frequently with the aid of a vibrating membrane or reed.

Examples of such prior art devices are shown in U.S. Pat. No. 3,747,127 to Taub; U.S. Pat. No. 3,952,335 to Sorce et al.; U.S. Pat. No. 4,060,856 to Edwards, and U.S. Pat. No. 4,223,411 to Schoendorfer et al.

One drawback to such devices is the need to provide a second surgical opening, or fistula, in the neck in order to direct the diverted air flow for speech around the surgically formed "pseudoglottis" mentioned above. While the surgical procedures used to form such fistulas are, more or less, routine, any additional surgery is, preferably, to be avoided, if possible.

Another disadvantage to such devices resides in the means used to discriminate between normal exhalation and a speech effort. For example, one class of external laryngeal prostheses, represented by a device disclosed in the above-referenced Edwards patent, requires the manual actuation of a valve which diverts air into the hypopharyngeal area when speech is desired. Such a mechanism is awkward to use, and it may be inoperable by patients with impaired use of their arms and hands.

Alternatively, devices such as those disclosed in the Taub, Sorce et al., and Schoendorfer et al. patents incorporate a pressure-discriminating mechanism which automatically distinguishes between a normal breathing effort and a speech effort. For example, the Schoendorfer et al. device uses a vibratory tone-generating mechanism which vibrates only when the user exhales above a preselected pressure, so that normal exhalation occurs silently. This device has no provision for allowing coughing or heavy breathing (as from physical exertion) without actuating the tone-generating mechanism. The Taub device uses a valve which normally opens a passageway for exhalation, but which closes the passageway in response to the increased pressure of a speech effort, so that exhaled air is diverted into an esophageal fistula for phonation via the esophageal mucosa. One drawback to the Taub device is that it does not allow the patient to cough freely or to breathe heavily without manual adjustment of the valve mechanism.

The Sorce et al. device uses a valve which allows exhalation through the tracheostoma at normal exhalation pressures and diverts exhaled air into the hypopharynx through a hypopharyngeal fistula at increased exhalation pressures indicative of a speech effort. The valve in this device allows the patient to cough freely by uncovering the normal exhalation passage through the tracheostoma in response to the high pressure generated by a cough. After a cough, however, the valve may require manual resetting to permit speech again. As with the Schoendorfer et al. device, sounds may be produced by heavy breathing, especially if a vibratory tone-generator is used.

From the foregoing discussion of the prior art, it can be seen that there is an as yet unfulfilled need for a laryngeal prosthesis which automatically discriminates between a normal breathing effort and a speech effort, and which allows the patient to cough freely, without the need for external manipulation either to select a mode of operation or to reset the device to an operable mode. In addition, there is a need for such a device which further discriminates automatically between a speech effort and a "heavy" breathing (gasping) effort, so that such heavy breathing is not accompanied by a tone. Moreover, there is lacking a device of this nature which is operable without an esophageal or hypopharyngeal fistula in addition to the tracheostoma. There is a further need for such a device which is simple of construction and relatively maintenance free. Finally, there is a need for a laryngeal prosthesis which not only includes the aforesaid features, but which also provides a suitable epiglottal function.

SUMMARY OF THE INVENTION

Broadly, the present invention is a self-contained, external laryngeal prosthesis, adapted for being fitted into a tracheostoma, and which includes a one-way inhalation valve, a one-way exhalation valve, a vibratory tone-generating mechanism in the exhalation flow path, means operatively connected to the tone-generating mechanism to disable it in response to either coughing or "heavy" breathing (gasping), and means for directing exhaled air into the hypopharynx through an incision in the surgically-formed pseudoglottis. The tone-generating mechanism includes means for discriminating between a normal exhalation and a speech effort, while the means for directing exhaled air includes a one-way valve which permits the entry of air into the hypopharynx, but which seals against the influx of food, secretions, etc.

More specifically, the invention includes a housing adapted to be fitted to the tracheostoma. A first or lower conduit in the lower part of the housing communicates with the trachea through the tracheostoma, and a second conduit in the upper part of the housing communicates with the hypopharynx through a cuffed tube which passes through an incision in the pseudoglottis. This cuffed tube terminates in the aforementioned one-way valve. The lower conduit enters the housing in a lower chamber defined at one end by the one-way inhalation valve, and at the other end by the one-way exhalation valve. Downstream from the exhalation valve is a vibratory tone-generating mechanism, which, preferably, includes a reed. The reed comprises a band of rigid material which is resiliently mounted so as to overlie a reed seat having an air passage therethrough. The reed seat, in turn, is mounted in a spring-biased carrier having a peripheral valving surface which normally seats against a concentric valve seat within the housing. Downstream of the carrier is an upper chamber into which the upper conduit enters.

Inhalation is performed through the inhalation valve and the lower conduit. Exhalation, be it normal, vocalizing, gasping, or coughing, is performed through the lower conduit and the exhalation valve. In normal exhalation, which generally occurs at pressure levels of less than 10 cmH$_2$O, exhaled air passes around the reed and through the passage in the reed seat into the upper chamber, from which it enters the upper conduit and the cuffed tube, exiting into the hypopharynx. The rigidity of the reed is such that there is little or no vibration at what may be termed "sub-phonation" pressure levels. Also, such pressure levels are insufficient to overcome the spring bias under which the carrier is held against its valve seat.

When speech is desired, the user will increase the expiratory effort to achieve a pressure level in the range of approximately 12 to 20 cmH$_2$O. This may be termed a "phonation" pressure level, and it is sufficient to cause the reed to vibrate with a tone having a frequency within the range of normal human speech. The phonation pressure level, however, is still insufficient to lift the carrier from its seat, so that the path of exhaled air is the same as with normal exhalation.

During or after physical exertion, the user may experience heavy breathing or gasping. Pressures developed during exhalation in such instances exceed 20 cmH$_2$O, and typically are in the range of 30 to 50 cmH$_2$O. Likewise, coughing typically produces instantaneous pressures in excess of 60 cmH$_2$O. At such pressure levels, the reed is caused to collapse against its seat, closing the passage therethrough. Sufficient pressure very quickly builds up upstream of the carrier to lift the carrier off its seat against the spring bias, thereby providing a clear flow path around the carrier into the upper chamber of the housing.

A preferred embodiment of the invention advantageously includes means for adjusting the spring bias of the carrier to allow the sensitivity to gasping or heavy breathing to be varied. Also advantageously included is means for adjusting the tension on the reed so that it is caused to vibrate and collapse, respectively, in the appropriate pressure ranges. Both of these adjustments are preferably made during the manufacture of the device, so that the preadjusted parameters are, more or less, fixed during its use.

From the foregoing, it can be seen that the present invention provides good discrimination between a normal exhalation effort and a vocalizing or speech effort, so that speech, when desired, is effected automatically at a pressure (effort) level that is relatively natural for the user. In addition, the device automatically switches to a silent mode of operation in response to heavy breathing ("panting" or "gasping"), even though such breathing efforts are at lower exhalation pressures than coughing. Thus, the "switching" between the normal breathing mode, the speaking mode, and the heavy breathing or coughing mode occurs entirely automatically, without the need for manual adjustment or manipulation. In addition, the device is easy to fit to the user, requiring no esophageal or hypopharyngeal fistula. Moreover, the invention permits relatively economical manufacture and simple maintenance.

These and other advantages of the invention will be more readily appreciated from the detailed description which follows.

DETAILED DESCRIPTION OF THE PREFERRED EMBODIMENT

Figure 1:
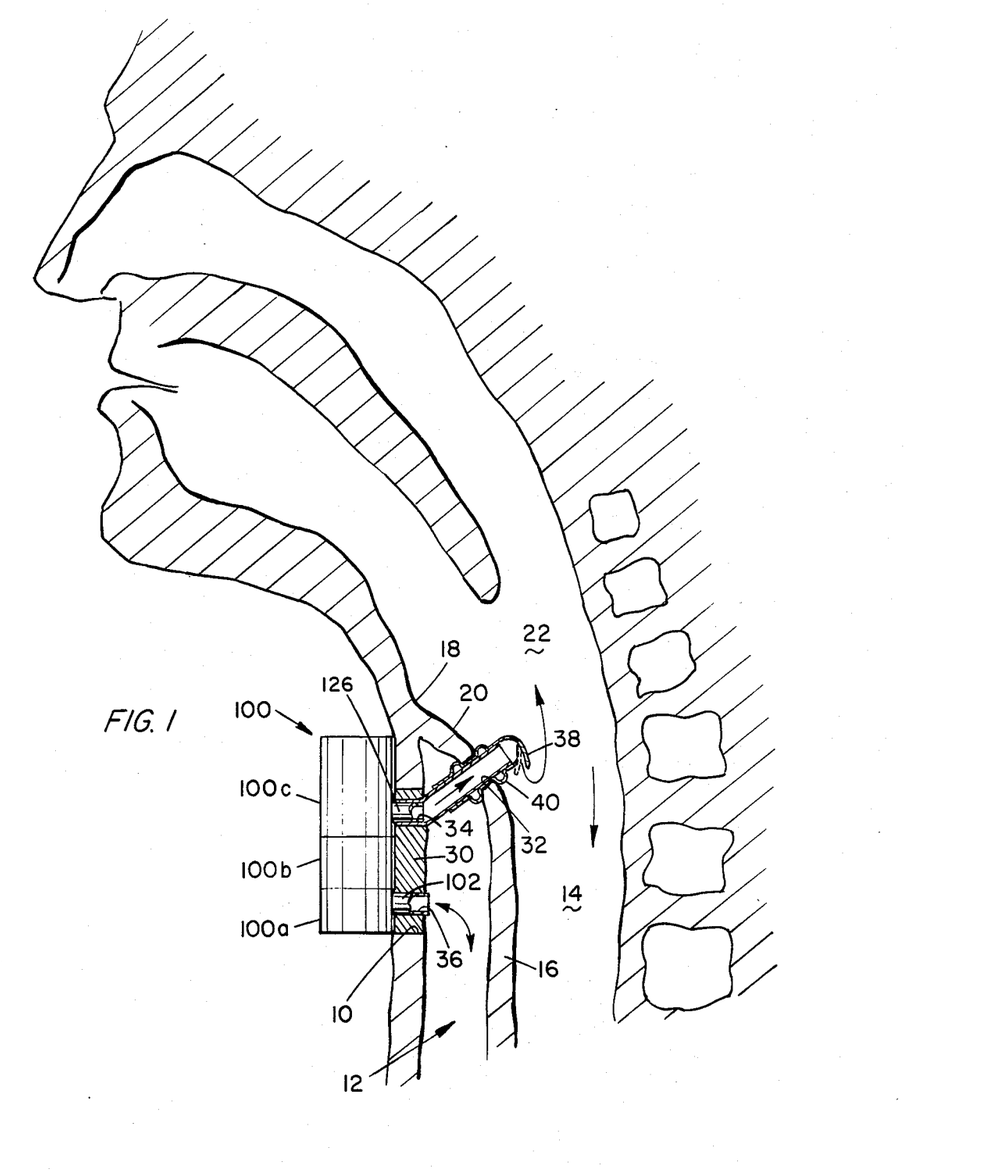
FIG. 1 is an elevational view partially in cross-section of a preferred embodiment of the invention, showing its tracheostoma fitting and its hypopharyngeal tube as installed in a patient or user.

Referring first to FIG. 1, a preferred embodiment of the present invention is shown installed in a human patient or user. As is usually the case with a laryngectomized patient, a tracheostoma 10 is made through the neck and into the trachea 12. The tissue separating the trachea 12 and the esophagus 14, which may be termed the tracheal-esophageal wall 16, is flapped over the end of the trachea 10 and sutured to the internal neck tissue, as at 18, to provide a "pseudoglottis" 20. The pseudoglottis 20 is a barrier between the trachea and the hypopharynx 22 to prevent the entry of food, saliva, mucous, etc. into the trachea. Other surgical techniques to provide such a pseudoglottis may also be used.

As can be seen from FIG. 1, the invention comprises two major subassemblies, which may be described as the internal and external subassemblies. The external subassembly comprises a housing 100 and the components contained therein, as will be described in detail later on. The internal subassembly comprises a sealing fitting 30 for the tracheostoma 10, and a hypopharyngeal tube 32 which extends from an upper passage 34 in the fitting 32, through an incision in the pseudoglottis 20, and into the hypopharynx 22. The fitting 30 also includes a lower passage 36.

The fitting 30 is configured to provide a sealing fit within the tracheostoma, and yet to be easily removable therefrom if desired. It can be made of any suitable biocompatible material.

A first end of the hypopharyngeal tube 32 is, as previously mentioned, inserted into the upper passage 34 in the fitting 30; the other or second end passing into the hypopharynx through the pseudoglottis. This second end of the tube 32 is provided with a one-way epiglottal valve 38. The valve 38 may have any of a number of specific configurations. As shown in FIG. 1, for example, it comprises a resilient flap which is normally in an open position (as shown by the solid outline), but which flexes to a closed position (dotted outline) when food or bodily secretions (such as saliva or mucous) pass over it. In this regard, it is advantageous to have the flap "hinged" to the tube at the flap's upstream side, as shown, so that the tube opening is shielded by the flap, which deflects food and secretions away from the tube opening.

Alternatively, a normally closed tricuspid valve may be used in place of the flapper valve 38. In either case, an epiglottal function is simulated.

The tube 32 has a pair of inflatable cuffs 40 disposed on either side of the pseudoglottis. The cuffs 40 retain the tube in place with minimal abrasion of the tissue. They are inflated via a lumen (not shown) in the tube wall, as is a standard practice with devices such as tracheostomy tubes and catheters.

Figure 2:
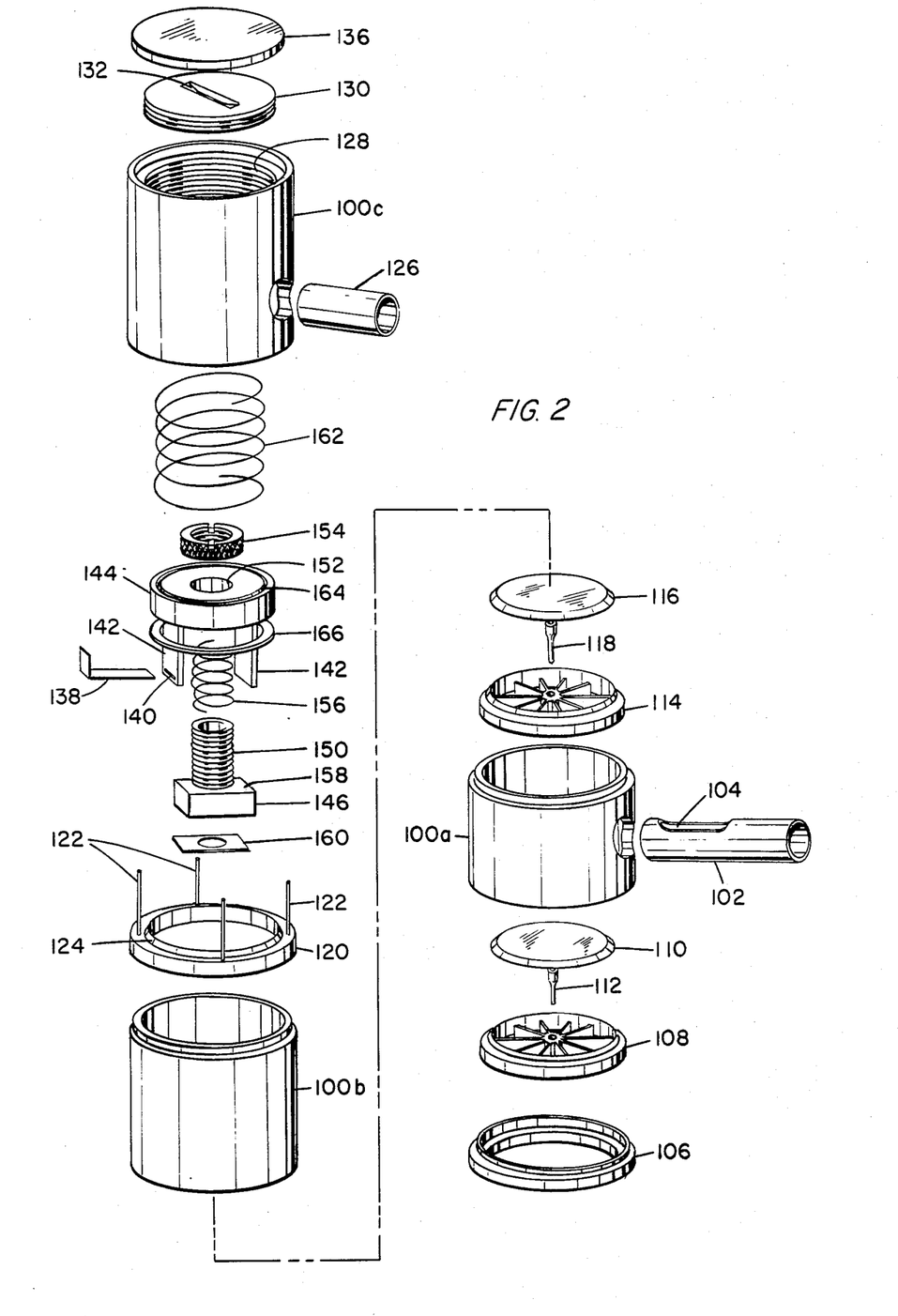
FIG. 2 is an exploded perspective view of that part of the preferred embodiment shown schematically in FIG. 1, namely the external housing and the components therein.

FIGS. 2 through 5 illustrate in detail the external subassembly, comprising the housing 100 and the components contained therein. As best shown in FIG. 2, the housing comprises three axially-aligned cylindrical segments 100a, 100b, and 100c attached end-to-end to form a hollow cylinder.

The first, or lower segment 100a has an aperture 102 in the side into which extends a first or lower conduit 104, itself having an elongate side-wall aperture or port 104. Situated within the housing segment 100a near its open lower end is a retaining ring 106 which retains an inhalation valve seat 108. Although shown as separate components, the retaining ring 106 and valve seat 108 may be formed as an integral unit.

Figure 3:
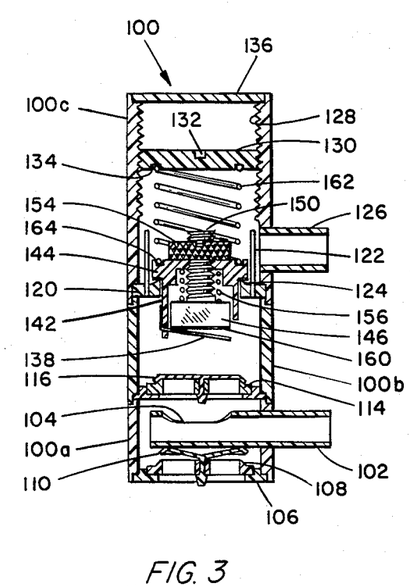
FIGS. 3, 4, and 5 are cross-sectional views of the external components of the preferred embodiment, showing the various modes of operation of the invention.

Seated in the valve seat 106 is a one-way inhalation valve 110 which allows gas to enter the housing through its lower open end (FIG. 3), but does not allow gas to pass outwardly therefrom. The valve 110 is a disc or diaphragm of highly pliable, resilient material which is held in the seat 108 by a central stem 112, and which flexes upwardly away from the seat around its edges in response to an incoming flow of air, as shown in FIG. 3.

At the upper end of the lower housing segment 100a is situated an exhalation valve seat 114, which seats an exhalation valve 116. The exhalation valve seat 114 and the exhalation valve 116 may advantageously be of the same type as the inhalation valve 110 and its seat 108. That is, the exhalation valve 116 comprises a highly flexible disc or diaphragm retained in the seat 114 by means of a central stem 118. The exhalation valve 116 allows gas to flow only upwardly through it; that is, out of the lower housing segment 100a and into the middle housing segment 100b.

Thus, as described above, the lower housing segment forms a first chamber defined between the inhalation valve 110 and the exhalation valve 116.

The lower end of the middle housing segment 100b is joined to the upper end of the lower housing segment 100a. Situated inside the middle housing segment 100b near its upper end is a sealing ring 120, which may advantageously include a plurality of upwardly-extending guide rods 122. The inner periphery of the sealing ring 120 is formed as an upwardly extending rim or bead 124. The middle housing segment 100b may thus be considered a second chamber defined between the exhalation valve 116 and the sealing ring 120.

Figure 4:
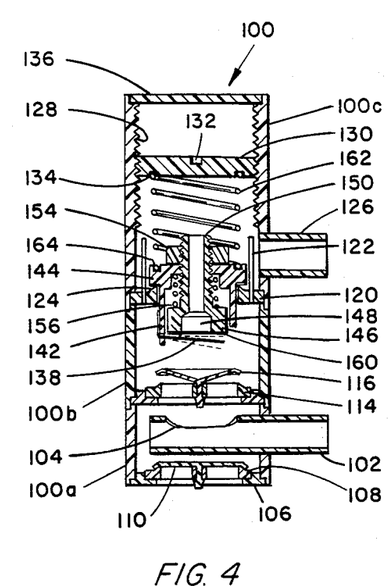
Figure 5:
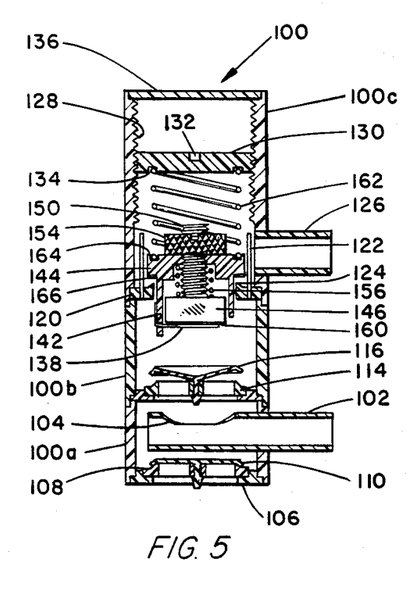

The lower end of the upper housing segment 100c is joined to the upper end of the middle housing segment 100b. The sidewall of the upper housing segment 100c is apertured at a suitable location to receive a second or upper conduit 126. That portion of the interior surface of the upper housing segment 100c above the upper conduit 126 is advantageously threaded, as at 128, for threaded engagement with an adjustment plate 130, the purpose of which will be explained below. The upper surface of the adjustment plate 130 may have a linear slot 132 to facilitate the adjustment of its position within the upper housing segment 100c, while the lower surface of the adjustment plate is advantageously provided with an annular groove 134 (FIGS. 3, 4, 5). The upper end of the upper housing segment 100c is sealed with an end cap 136. A third chamber is thus defined between the end cap 136 and the sealing ring 120.

The vibratory tone-generating mechanism of the preferred embodiment comprises a reed 138, formed from an L-shaped band of a suitable metal. A band formed of stainless steel with a thickness of approximately 5 mils has produced good results, although other materials (metallic and nonmetallic) and thicknesses may also be acceptable.

The reed 138 is retained in a slot 140 formed in one of two diametrically-opposed legs or posts 142 extending downwardly from an annular reed carrier 144. The posts 142 serve to locate the carrier 144 within the central opening of the sealing ring 120, and they should be long enough to stay within said opening at the upper extreme of the carrier's travel, as will be explained below.

The reed 138 overlies the flat surface of a reed seat 146, the latter having a central aperture 148 (FIG. 4) communicating with the hollow interior of a threaded shaft 150. The shaft 150 passes through a central aperture 152 in the carrier 144 (FIG. 2), and it is held in a preselected position with respect to the carrier by a threaded nut 154 and a retaining spring 156, the latter engaging the underside of the carrier and a shoulder 158 (FIG. 2) formed around the bottom terminus of the threaded shaft 150. The surface of the reed seat 146 which underlies the reed 138 is advantageously covered by a gasket 160 formed of a soft material, such as a rubber or a soft plastic.

The nut 154 is used to adjust the position of the reed seat 146 with respect to the carrier 144 such that one edge of the reed seat engages the reed 138 and pushes it away from the reed seat, as shown in FIGS. 3, 4, and 5. The reed 138 is thus biased so that, when properly adjusted, it vibrates with an audible frequency at exhalation pressures corresponding to normal speech efforts, and it collapses against the gasket 160 at pressures in excess of speech levels, as explained in greater detail below.

The carrier 144 is biased downwardly by a main-spring 162 which is seated in the groove 134 of the adjustment plate 130 and in a similar annular groove 164 in the upper surface of the carrier. On the underside of the carrier, opposite the groove 164, is an annular gasket 166 (FIGS. 2 and 5). The carrier 144, as will be seen below, functions as a valve body biased in a normally closed position by the main spring 162 so that the gasket 166 engages the bead 124 of the sealing ring 120 (FIGS. 3 and 4). The adjustment plate 130 is used to selectably adjust the pressure at which the carrier is lifted off of the bead 124, thereby resulting in an open valve position. This pressure is selected to be that at which the coughing or gasping mode is to be initiated, as will be explained below.

Advantageously, both the nut 154 and the adjustment plate 130 may be adjusted to their selected positions during manufacture, and then fixed in place, as by a suitable adhesive or by ultrasonic welding. Toward this end, both the nut 154 and the adjustment plate 130 are advantageously formed of the same material as the other parts of housing and its associated components (except the reed 138 and the springs 156 and 162). Preferably, this material is a biocompatible plastic, such as a polysulfone.

OPERATION

Referring once again to FIG. 1, it can be seen that when the invention is in use, the housing 100 is installed in the fitting 30 with the lower conduit 102 communicating with the lower passage 36, and the upper conduit 126 in communication with the upper passage 34. This puts the first or lowermost chamber in the housing in communication with the user's lungs through the trachea 12, and the third or uppermost chamber of the housing in communication with the hypopharynx through the tube 32.

The operation of the invention is best understood with reference to FIGS. 3, 4, and 5, which show the various operational modes of the external subassembly of the invention.

First, FIG. 3 shows the invention during inhalation. In response to an inhalation effort by the user, air is drawn through the open bottom of the lower housing segment 100a and into the lowermost chamber of the housing through the inhalation valve 110. From there, the air enters the lower conduit 102 through the port 104, for delivery to the user's lungs via the lower passage 36 of the fitting 30 and the trachea (FIG. 1). The exhalation valve 116 remains closed, as shown.

FIG. 4 shows the invention during the normal exhalation mode and during the speaking mode. In both of these modes of operation, exhaled gas passes through the lower conduit 102 into the lowermost chamber of the housing. From there, the exhalation valve 116 admits the air into the second or middle chamber of the housing, while the inhalation valve 110 remains closed.

As previously discussed, normal exhalation usually occurs at peak pressure levels of less than 10 centimeters of water (cmH$_2$O). With the reed 138 biased by the edge of the reed seat 146 as described above, the reed 138 is spaced from the reed seat gasket 160, leaving a gap which communicates with the air passage formed by the reed seat aperture 148 and the hollow bore of the threaded shaft 150. By appropriate manipulation of the nut 154, the tension on the reed 138 can be selectably adjusted so that it remains substantially stationary (as shown in the solid outline in FIG. 4) at sub-phonation pressure levels, i.e., less than approximately 10 cmH$_2$O.

Likewise, if the tension on the reed has been appropriately adjusted, the pressure levels produced by a speech effort (typically 12 to 20 cmH$_2$O) will cause the reed to vibrate, as shown by the dotted lines in FIG. 4. By judicious selection of the reed material, thickness, and tension, the reed will vibrate with an audible tone within the frequency range of normal speech (i.e., between approximately 100 Hz and 400 Hz). The gasket 160, being of a softer, more resilient material than the reed seat 146, serves to muffle any unpleasant noises or sounds created when the reed strikes the reed seat during vibration.

During both the normal exhalation and speech modes (i.e., at sub-phonation and phonation pressure levels), air passing over and around the reed is conducted through a principal flow path, comprising the reed seat aperture 148 and the bore of the hollow threaded shaft 150, into the uppermost chamber of the housing. From there, the exhaled air passes through the upper conduit 126 and the upper passage 34 of the fitting 30, and into the hypopharyngeal tube 32 (FIG. 1). The air then exits into the hypopharynx through the epiglottal valve 38. During the speaking mode, the vibrations of the reed 138 are transmitted to the air passing into the hypopharynx, and it is this vibrating air that is modulated by the pharyngeal and buccal structures, including the tongue and lips, to produce speech.

During heavy breathing (gasping or panting) and coughing, it is usually desirable to disable the tone-generating mechanism to avoid the production of possibly annoying or embarrassing noises. This mode of operation, which may be termed the "coughing" mode, is illustrated in FIG. 5.

As in the normal exhalation and speech modes, exhaled air passes into the middle chamber of the housing via the lower conduit 102, and the port 104, and the exhalation valve 116, with the inhalation valve 110 remaining closed. The pressures generated by heavy breathing and coughing are typically well in excess of 20 cmH$_2$O. By appropriate selection of the tension on the reed 138 (as adjusted by the nut 154), the reed can be caused to collapse against the reed seat gasket 160, blocking the aperture 148, when such pressure levels are reached. Pressure then very quickly builds in the second chamber to a level sufficient to overcome the bias of the main spring 162, thereby lifting the carrier 144 upwardly. This allows air to pass through the central aperture of the sealing ring 120 and between the gap that is created between the bead 124 on the sealing ring and the valving surface (gasket 166) of the carrier. Air thus enters the uppermost chamber of the housing through a secondary flow path without actuation of the tone-generating mechanism. The air then travels into the hypopharynx in the manner described above, to be exhausted from the body via the nose and/or mouth. The collapsing of the reed and the lifting of the carrier thus, effectively, removes the operative part of the tone-generating mechanism from the stream of the exhalation air flow. The pressure level at which this coughing mode is initiated can be selected, as previously described, by adjusting the compression of the mainspring 162 via the adjustment plate 130.

After each exhalation in this manner, the carrier 144 is returned to its "closed" position (i.e., the bead 124 engaging the gasket 166) by the force of the mainspring 162. During this oscillatory movement of the carrier 144, the downwardly-extending posts 142 guide the carrier and maintain its proper alignment in the interior of the sealing ring 120. Thus, the posts 142 must be of sufficient length to remain within the ring's interior at the uppermost extreme of the carrier's travel, as previously mentioned.

As discussed above, the adjustments of the reed tension and the mainspring compression may be preselected during manufacture, with the nut 154 and the adjustment plate 130 being thereafter fixed in their respective preselected positions. In this manner, devices in accordance with the present invention can be specifically adjusted for different types of users. For example, small children may require different settings of these adjustments from those required by adults.

From the foregoing description, it can be seen that the present invention provides many significant advantages. Specifically, good discrimination is provided between the various modes of operation, and switching between these modes occurs automatically, and in a manner which closely simulates the natural functions. Moreover, installation of the present invention is surgically simple, requiring only the pseudoglottal incision in addition to the tracheostomy. Furthermore, it can be appreciated that the construction of the present invention allows for economy of manufacture, and ease of use and maintenance. Still another advantage resides in the facility with which the external subassembly can be removed from the fitting 30 for cleaning and maintenance, or when extended periods of heavy breathing are anticipated, leaving the user to breathe through the tracheostoma via the passages 34 and 36 in the fitting.

While a specific preferred embodiment of the invention has been described, it should be understood that various modifications may suggest themselves to those skilled in the pertinent arts. For example, the housing may take a variety of forms, and may be of one piece, instead of the three-piece cylindrical structure shown. Also, the internal components within the housing may be modified from the specific configurations shown while maintaining their operative characteristics. Such modifications should be considered within the spirit and scope of the invention, as defined in the claims which follow.

What is claimed is:

1. A laryngeal prosthesis for a tracheostomized patient having a surgically-formed pseudoglottis between the trachea and the hypopharynx, said prosthesis comprising:
   a housing;
   a fitting adapted for sealingly attaching said housing to the exterior of the tracheostoma formed in said patient's neck;
   first passage means adapted for communicating between said housing and the trachea through said fitting;
   inhalation valving means in said housing for permitting the flow of air from outside said housing in said housing and through said first passage means;
   second passage means adapted for communicating between said housing and the hypopharynx of said patient;
   exhalation valving means in said housing for permitting the flow of exhaled air received from said first passage means toward said second passage means;
   first pressure-responsive means in said housing downstream from said exhalation valving means and upstream from said second passage means for (a) generating an audible tone in response to air pressures only within a predetermined pressure range, and (b) permitting the passage of exhaled air from said exhalation valving means to said second passage means only in response to air pressures below a preselected pressure, said preselected pressure being at least approximately equal to the upper limit of said predetermined pressure range; and
   second pressure responsive means for allowing the passage of air from said exhalation valving means to said second passage means only in response to air pressures above said preselected pressure.

2. The laryngeal prosthesis of claim 1, wherein said second passage means includes a first end in said housing, a second end adapted for insertion into the hypopharynx, and means at said second end for blocking the flow of material into said second passage means from the hypopharynx.

3. The laryngeal prosthesis of claim 2, wherein said second end is adapted for insertion through, and retention in, an incision in the pseudoglottis.

4. The laryngeal prosthesis of claim 1, wherein said first pressure-responsive means comprises:
   third passage means communicating between said exhalation valving means and said second passage means;
   a vibratory member overlying the upstream entry of said third passage means; and
   tensioning means for resiliently biasing said vibratory member so that said vibratory member vibrates with said audible tone only in response to pressures within said predetermined pressure range and collapses against said upstream entry of said third passage means to block the passage of air therethrough in response to air pressures above said preselected pressure.

5. The laryngeal prosthesis of claim 1, wherein said second pressure-responsive means comprises:
   carrier means operatively connected to said first pressure-responsive means and having a first valving surface thereon;
   means in said housing defining a second valving surface engageable with said first valving surface; and
   means in said housing for biasing said carrier means to engage said first valving surface against said second valving surface, and to allow the disengagement of said first and second valving surfaces to open an air passage therebetween at pressures above said preselected pressure.

6. The laryngeal prosthesis of claim 4, further comprising carrier means operatively connecting said third passage means, said vibratory member, and said tensioning means, and wherein said third passage means comprises:
   means defining a substantially flat surface underlying said vibratory member and having an aperture therethrough forming said upstream entry of said third passage means; and
   a shaft connecting said surface-defining means to said carrier means and having a hollow bore therethrough communicating with said aperture.

7. The laryngeal prosthesis of claim 6, wherein said vibratory member is a reed, and wherein said tensioning means comprises means for adjusting the angle between said reed and said substantially flat surface.

8. The laryngeal prosthesis of claim 6, wherein said second pressure-responsive means comprises:
   a first valving surface on said carrier means;
   a second valving surface in said housing; and
   biasing means, acting on said carrier means, for urging said first valving surface into engagement with said second valving surface and allowing the disengagement of said first and second valving surfaces to provide an air passage therebetween at pressures greater than said preselected pressure.

9. The laryngeal prosthesis of claim 1, further comprising means for adjusting said preselected pressure.

10. The laryngeal prosthesis of claim 1, further comprising means for varying said predetermined pressure range.

11. A laryngeal prosthesis for a tracheostomized patient having a surgically-formed pseudoglottis between the trachea and the hypopharynx, said prosthesis comprising:
- a housing;
- a fitting adapted for sealingly attaching said housing to the exterior of a tracheostoma formed in the patient's neck;
- a first conduit adapted for communicating between said housing and the trachea through said fitting;
- an inhalation valve in said housing for permitting the flow of ambient air into said first conduit;
- a second conduit adapted for communicating between said housing and the hypopharynx of said patient;
- an exhalation valve in said housing for permitting the flow of exhaled air received from said first conduit toward said second conduit;
- means defining a principal flow path between said exhalation valve and said second conduit;
- first pressure-responsive means associated with said principal flow path defining means for (a) generating an audible tone in response to air pressures within a predetermined pressure range, and (b) closing said principal flow path in response to pressures exceeding a preselected pressure, said preselected pressure being at least approximately equal to the upper limit of said predetermined pressure range;
- means defining a secondary flow path between said exhalation valve and said second conduit; and
- second pressure-responsive means normally closing said secondary flow path and opening said secondary flow path at pressures exceeding said preselected pressure.

12. The laryngeal prosthesis of claim 11, wherein said second conduit comprises:
- a first end communicating with the interior of said housing through said fitting;
- a second end adapted for insertion into the hypopharynx through an incision in the pseudoglottis;
- means on said conduit intermediate said first and second ends for retaining said conduit in place in said incision;

and
- means at said second end of said conduit adapted for blocking the entry of material into said conduit from the hypopharynx.

13. The laryngeal prosthesis of claim 11, wherein said principal flow path defining means includes a hollow member having upstream and downstream openings, and said first pressure-responsive means comprises:
- a vibratory member proximate said upstream opening;

and
- tensioning means for resiliently biasing said vibratory member so that said vibratory member vibrates with said audible tone in response to air pressures within said predetermined pressure range and blocks said upstream opening in response to air pressures exceeding said preselected pressure.

14. The laryngeal prosthesis of claim 11, wherein said secondary flow path defining means includes an apertured member having a first valving surface around the aperture therethrough, and said second pressure-responsive means comprises:
- valving means having a second valving surface engageable with said first valving surface to close said secondary flow path; and
- means for biasing said valving means so that said first and second valving surfaces disengage at pressures above said preselected pressure, thereby opening said secondary flow path.

15. The laryngeal prosthesis of claim 11, further comprising means for adjustably varying said preselected pressure.

16. The laryngeal prosthesis of claim 11, further comprising means for adjustably varying said predetermined pressure range.

17. The laryngeal prosthesis of claim 13, wherein said secondary flow path defining means includes an apertured member in said housing having a first valving surface around the aperture therethrough;
- carrier means, operatively connecting said hollow member, said vibratory member, and said tensioning means, and having a second valving surface engageable with said first valving surface; and
- biasing means, acting on said carrier means, for urging said second valving surface into engagement with said first valving surface to close said secondary flow path, and for allowing the disengagement of said first and second valving surfaces at pressures greater than said preselected pressure to open said secondary flow path.

18. The laryngeal prosthesis of claim 17, wherein said vibratory member is a reed attached to said carrier means, said hollow member includes a flat surface around said upstream opening and is attached to said carrier means so that said reed is positioned over, and spaced from, said flat surface and said upstream opening at pressures within said predetermined pressure range, and said tensioning means biases said reed so that said reed vibrates with an audible tone in response to air pressures within said predetermined pressure range, and collapses against said surface to block said upstream opening in response to pressures greater than said preselected pressure.

19. The laryngeal prosthesis of claim 18, wherein said tensioning means includes means for adjustably varying the bias applied to said reed so as to vary said predetermined pressure range.

20. A laryngeal prosthesis for a tracheostomized patient having a surgically-formed pseudoglottis between the trachea and the hypopharynx, said prosthesis comprising:
- a housing;
- a fitting adapted for sealingly attaching said housing to the exterior of a tracheostoma formed in the patient's neck;
- first conduit means adapted for communicating between said housing and the trachea through said fitting;
- second conduit means adapted for communicating between said housing and the hypopharynx through said fitting and an incision in the pseudoglottis;
- valving means in said housing for directing air into said first conduit means in response to inhalation by the patient, and for directing exhaled air from said first conduit means toward said second conduit means;
- tone-generating means in said housing downstream from said valving means and upstream from said second conduit means for generating an audible tone in response to air pressures within a predetermined pressure range; and pressure-responsive means in said housing and operatively connected to said tone-generating means for (a) disabling said tone-generating means in response to pressures greather than a preselected pressure at least approximately equal to the upper limit of said predetermined pressure range, and (b) reenabling said tone-generating means in response to a return to pressures within said predetermined pressure range.

21. The laryngeal prosthesis of claim 20, wherein said valving means comprises:

an inhalation valve in said housing adapted to permit the flow of ambient air into said first conduit means in response to inhalation; and an exhalation valve in said housing downstream from said inhalation valve and adapted to permit the flow of exhaled air from said first conduit means toward said second conduit means, said second conduit means being downstream from said first conduit means.

22. The laryngeal prosthesis of claim 20, wherein said second conduit means comprises:

a hollow tube having a first end in communication with the interior of said housing, and a second end adapted for passage through said incision in the pseudoglottis into the hypopharynx; and means at said second end of said tube for simulating an epiglottal function.

23. The laryngeal prosthesis of claim 20, wherein said tone-generating means includes means forming a principal air flow passage from said valving means to said second conduit means, said tone-generating means producing said audible tone in response to the flow of air through said principal passage, and wherein said pressure-responsive means is responsive to pressures greater than said preselected pressure by (a) closing said principal passage, and (b) opening a secondary air flow passage from said valving means to said second conduit means.

24. The laryngeal prosthesis of claim 23, wherein said pressure-responsive means is responsive to a return to pressures in said predetermined range from pressures exceeding said preselected pressure by (a) opening said principal passage, and (b) closing said secondary passage.

25. The laryngeal prosthesis of claim 24, wherein said tone-generating means comprises:

a vibratory member;

means defining said principal air flow passage and including a surface underlying said vibratory member; and tensioning means for resiliently biasing said vibratory member so that said vibratory member vibrates with an audible frequency in response to air pressures within said predetermined pressure range.

26. The laryngeal prosthesis of claim 25, wherein said tensioning means further biases said vibratory member so that said vibratory member collapses against said underlying surface to block said principal air flow passage in response to air pressures greater than said preselected pressure, and wherein said pressure-responsive means comprises;

said tensioning means;

first means in said housing having a first valving surface thereon;

second means in said housing having a second valving surface thereon engageable with said first valving surface; and third means for biasing said second means against said first means to engage said first and second valving surfaces, and allowing the disengagement of said first and second valving surfaces to open said secondary air flow path therebetween in response to air pressures greater than said preselected pressure.

27. A laryngeal prosthesis for a tracheostomized patient having a surgically-formed pseudoglottis between the trachea and the hypopharynx, said prosthesis comprising:

a housing;

a fitting adapted for sealingly attaching said housing to the exterior of a tracheostoma formed in the patient's neck;

a first conduit adapted for communicating between said housing and the trachea through said fitting;

an inhalation valve in said housing for permitting the flow of ambient air into said first conduit;

an exhalation valve in said housing downstream from said inhalation valve and defining a first chamber therebetween;

an annular member in said housing downstream from said exhalation valve and having a first valving surface thereon;

a movable closure member having a first portion extending through said annular member toward said exhalation valve, and a second portion including a second valving surface engageable against said first valving surface, said closure member and said annular member defining the downstream end of a second chamber in said housing and the upstream end of a third chamber in said housing, said exhalation valve thereby defining the upstream end of said second chamber;

means defining a principal air flow passage through said closure member from said second chamber to said third chamber, said principal passage having an upstream opening in said second chamber;

a vibratory member in said second chamber overlying and spaced from said upstream opening of said principal passage;

tensioning means for resiliently biasing said vibratory member, so that said vibratory member vibrates with an audible tone in response to air pressures within a predetermined pressure range, and said vibratory member is urged against said upstream opening to block said principal air flow passage in response to pressures greater than a preselected pressure at least approximately equal to the upper limit of said pressure range;

biasing means in said third chamber and acting on said closure member to urge said second valving surface into engagement with said first valving surface and to allow the disengagement of said first and second valving surfaces in response to air pressures greater than said preselected pressure, thereby to provide a secondary air flow passage from said second chamber to said third chamber; and a second conduit adapted for communication between said third chamber and the hypopharynx through said fitting and through an incision in said pseudoglottis.

* * * * *